United States Patent [19]

Cheng et al.

[11] Patent Number: 4,929,556

[45] Date of Patent: May 29, 1990

[54] ENZYME IMMOBILIZATION WITH POLYSULFONIUM SALTS

[75] Inventors: Roberta C. Cheng; Ritchie A. Wessling; Donald L. Schmidt, all of Midland, Mich.

[73] Assignee: The Dow Chemical Company, Midland, Mich.

[21] Appl. No.: 216,916

[22] Filed: Jul. 8, 1988

Related U.S. Application Data

[63] Continuation-in-part of Ser. No. 826,639, Feb. 6, 1986, abandoned.

[51] Int. Cl.$^5$ ............... C12N 11/08; C12N 9/92; C12N 11/04; C12P 19/24
[52] U.S. Cl. ................... 435/180; 435/94; 435/177; 435/181; 435/182; 435/234
[58] Field of Search ............. 435/94, 174, 177, 180, 435/181, 182, 234

[56] References Cited

U.S. PATENT DOCUMENTS

| | | | |
|---|---|---|---|
| 3,935,068 | 1/1976 | Nystrom | 435/94 |
| 4,217,215 | 8/1980 | Panzer et al. | 210/736 |
| 4,250,267 | 2/1981 | Hartdegan et al. | 435/182 X |
| 4,337,313 | 6/1982 | Hershberger et al. | 435/177 |
| 4,528,384 | 7/1985 | Schmidt et al. | 562/589 X |
| 4,659,665 | 4/1987 | Freeman et al. | 435/182 |
| 4,704,324 | 11/1987 | Davis et al. | 428/308.4 |

OTHER PUBLICATIONS

Zaborsky, O., Immobilized Enzymes, CRC Press, Cleveland, Ohio, 1973, pp. 70–74.

*Primary Examiner*—David M. Naff

[57] ABSTRACT

Polysulfonium salts that can react with nucleophilic groups and covalently cross-link are used to immobilize enzymes or enzyme-containing cellular material. Some of the polysulfonium salts can both flocculate and covalently cross-link. Replacement of the cross-linker, glutaraldehyde, with the polysulfonium salt results in greater retention of enzyme activity during immobilization. Immobilization is carried out by forming a mixture of an enzyme or enzyme-containing cellular material and the polysulfonium salt and subjecting the mixture to conditions such that sulfonium ions react with nucleophilic groups contained by the enzyme or cellular material to form a covalently cross-linked and water insoluble product. The enzyme or cellular material may be flocculated with a flocculating agent prior to cross-linking with the polysulfonium salt. The polysulfonium salt can be a polymer containing sulfonium groups.

10 Claims, No Drawings

ENZYME IMMOBILIZATION WITH POLYSULFONIUM SALTS

CROSS-REFERENCE TO A RELATED APPLICATION

The present application is a continuation-in-part application of U.S. application Ser. No. 826,639, filed Feb. 6, 1986 now abandoned.

BACKGROUND OF THE INVENTION

The subject invention relates to enzymatic processes for the preparation of specialty chemicals, e.g., for the preparation of fructose (levulose). Those skilled in this art have found that immobilization of a particular enzyme which catalyzes an enzymatic reaction, whether in the whole microbial cell or in cell-free systems, e.g. the enzyme or cellular material containing the enzyme, generally results in better yield of the desired product and an improvement in enzyme stability. This immobilization step can be accomplished by a number of procedures well known to those skilled in the art. Patents relating to the immobilization of enzymes can be exemplified as follows:

U.S. Pat. No. 3,779,869—Glucose isomerase within bacterial cells can be stabilized by glutaraldehyde treatment.

U.S. Pat. No. 3,935,068—Cationic polyelectrolytes are used for enzyme immobilization.

U.S. Pat. No. 3,980,521—Microbial cells are concentrated and cross-linked with glutaraldehyde to form a coherent solid product.

U.S. Pat. No. 4,288,552—Intracellular glutaraldehyde sensitive enzymes are immobilized by reacting microbial cell material with glutaraldehyde in the presence of a polyamine.

An important part of the immobilization process frequently involves the flocculation of microbial cells or cellular material, typically followed by cross-linking of the resulting flocculated cells or cellular material in order to obtain an immobilized enzyme which is easier to work with and which has improved enzyme stability (see U.S. Pat. Nos. 4,337,313; 3,821,086; 3,989,596; 3,935,068 and 3,935,069).

Flocculation is used to increase the aggregation of small particulate matter, such as microbial cells, cellular materials containing enzymes or the enzymes themselves, contained in an aqueous environment, for example, through coacervation or precipitation. Increasing the aggregation of the small particulate matter facilitates removal of the water. Although a flocculation step is generally unnecessary, the greater ease of water removal prior to cross-linking which can be accomplished by employing a flocculation step typically makes a flocculation step prior to cross-linking desirable.

Flocculation of microbial cells or cellular materials can be accomplished by use of a cationic polyelectrolyte, for example, polyamines, cationic polyaminoacids, cationic polyacrylamides, cationic poly(vinyl chloride), cationic copolymers, and cationic flocculants.

Cross-linking is used to impart more dimensional stability to the microbial cells or cellular materials being cross-linked. The prior art discloses the use of various di- or multi-functional cross-linking reagents. Few of these reagents are useful in large scale applications. Currently, glutaraldehyde is the cross-linker of choice due to its low cost, high reactivity and the good stability of its end products. (See U.S. Pat. Nos. 3,980,521, 4,288,552 and 4,355,105). However, glutaraldehyde has some drawbacks. Generally, the loss of enzyme activity resulting from glutaraldehyde cross-linking is significant even under mild conditions. Thus, there exists a need for milder and more specific cross-linkers for enzyme applications. Further, if the flocculation and cross-linking steps can be performed by a single reagent, obvious economic advantages in the immobilization process would be realized.

BRIEF SUMMARY OF THE INVENTION

The subject invention concerns a method of enzyme immobilization using materials containing reactive sulfonium groups (hereinafter frequently referred to as "polysulfonium salts") as cross-linking agents. Depending upon the nature of the polysulfonium salt selected, the polysulfonium salt can function solely as an enzyme cross-linker or serve the dual role of flocculant and cross-linker. The preferred invention process comprises mixing the enzyme-producing microbial cells, or cellular materials containing the enzymes to be immobilized, with a flocculating agent, which can be either a sulfonium polyelectrolyte or a non-sulfonium cationic polyelectrolyte, and cross-linking the solid with one or more polysulfonium salts. The cross-linking reaction is accelerated by removal of water from the mixture and by mild heating, such as up to about 75° C. Typically, it is carried out at temperatures between about 50° to 70° C. and under reduced pressure, typically <1 mm Hg. When a polysulfonium salt can function both as a flocculant and a cross-linker, the cross-linking step is simplified by merely heating and dehydrating the flocculated solid materials; no additional cross-linker is needed. Though flocculation is not a necessary step in the immobilization process, it greatly facilitates the separation of the cellular materials from the liquid when such cells are present in an aqueous environment, for example, fermentation broths. Moreover, other components, such as stabilizers, chelating agents, fibers, fillers and the like, which may be present in the slurry, can also be coflocculated with the enzyme or the cells. Thus, it is advantageous to include the flocculation step in the process.

The advantages of the invention process are two-fold: (1) the cross-linking reaction with a polysulfonium salt can be achieved under mild conditions with minimum loss of enzyme activity; and (2) certain polysulfonium salts can serve the dual role of flocculant and cross-linker, thus simplifying the immobilization process.

DETAILED DISCLOSURE OF THE INVENTION

POLYSULFONIUM SALTS AS CROSS-LINKERS

The cross-linking reaction according to the subject invention is carried out under reaction conditions such that the sulfonium groups present in the polysulfonium salt react strongly, e.g. covalently, with certain nucleophilic moieties present in the mixture, including nucleophilic groups attached to the polysulfonium salt, the flocculant, and the enzyme or cells to be immobilized, resulting in water-insoluble products. These water-insoluble products can be formed with minimal loss of enzyme activity. The optimum conditions for the cross-linking reactions are: pH 7–12, preferably 8–10; and temperatures from about 15°–100° C., preferably from about 40°–75° C., and most preferably from about 50°–70° C.

Polysulfonium cross-linkers are typically either low molecular weight (<5,000, and preferably <1,000), hydrophilic compounds bearing 2 to about 5, preferably 2 or 3 sulfonium groups; or amphoteric compounds bearing an approximately equal number of sulfonium groups and pH-dependent anionic nucleophilic groups, so that a relatively neutral charge is present. Amphoteric or zwitterion compounds when used as cross-linkers should be at or near the isoelectric point, that is, at a pH where the number of ionized anionic groups is approximately equal to the number of sulfonium groups. The amphoteric compounds may be low molecular weight polysulfonium zwitterions of molecular weight less than 5,000 or copolymers of molecular weight ranging from about 1,000 to 10,000,000.

The polysulfonium salt compounds are water compatible, that is, water soluble or water dispersible, and are chemically reactive towards nucleophiles (such as amino, alkoxide, or carboxyl groups). This chemically reactive property of the polysulfonium salt compounds results in the formation of covalent bonds with loss of charge during the process. They undergo polymerization or cross-linking preferentially with little fragmentation in alkaline (pH<7) solutions to form stable products. Most importantly, cross-linking of enzymes or cells with the polysulfonium cross-linkers results in minimal loss of enzyme activity. For example, cross-linking of Ampullariella-3876, ATCC 31351 (U.S. Pat. No. 4,308,349) (glucose isomerase-producing organism) with the sulfonium zwitterion derived from bisphenol A (I)

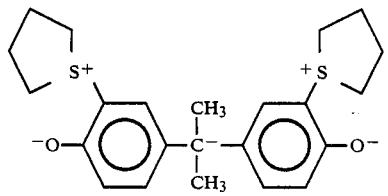

gives 60–90 percent retention of glucose isomerase activity (compared to 30–50 percent with glutaraldehyde). See Table 1 for the comparison of glutaraldehyde and sulfonium zwitterion cross-linking of Ampullariella-3876. Examples of suitable polysulfonium salts are as follows:

(1) Aryl cyclic sulfonium zwitterions having the following general structure (II):

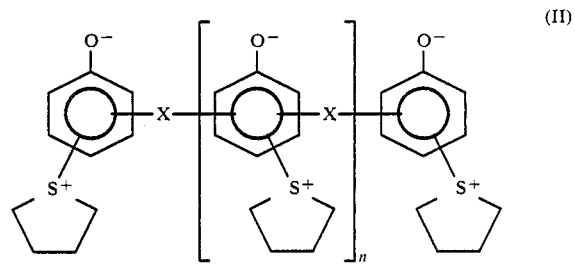

wherein n represents an integer of from 0 through 5; and X represents a covalent bond,

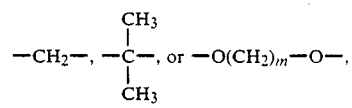

in which m is an integer of from 1 through 6.

(2) Copolymers containing hydroxyethyl methacrylate (HEMA)/sulfonium monomer/carboxylate monomer, where the ratio of sulfonium to carboxylate is approximately one; examples (V, VI, VII) are shown below:

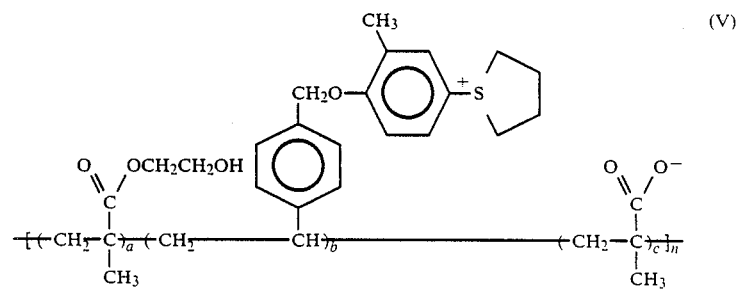

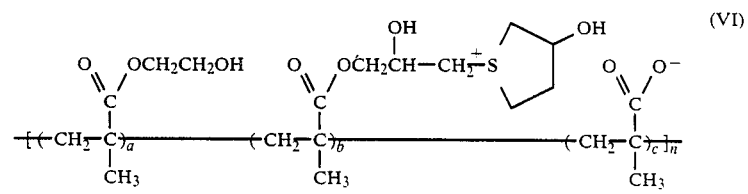

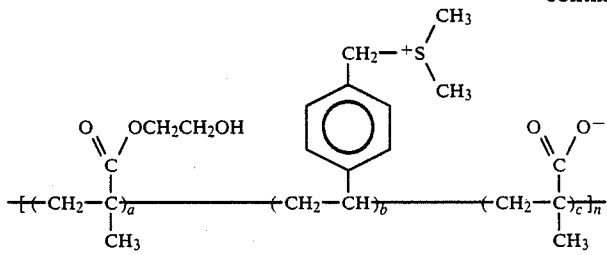

(VII)

wherein formulas V, VI and VII; a+b+c=1, n represents an integer of from 10 through 50, and b is approximately equal to c.

Flocculants which can be used in conjunction with the polysulfonium salt cross-linkers in the subject invention are cationic polyelectrolytes, for example, polyamines (primary, secondary, tertiary, and quaternary amines); cationic polyaminoacids, for example, polylysine; cationic polyacrylamides, for example, polydimethylaminopropylmethacrylamide; cationic poly(vinyl chloride), for example, poly(vinyl chloride) aminated with triethylene tetraamine; cationic copolymers, for example, styrenedimethylaminopropylmethacrylamide (50:50) copolymer; and cationic flocculants, for example, Purifloc C-31 TM (Trademark of The Dow Chemical Company, Midland, Mich.). The preferred amounts of flocculant and sulfonium cross-linker are about 1 percent to about 50 percent flocculant preferably 1 percent to about 15 percent, and about 4 percent to about 20 percent polysulfonium cross-linker, based on the dry weight of cellular material.

POLYSULFONIUM SALTS AS FLOCCULANTS AND CROSS-LINKERS

Polysulfonium flocculant cross-linkers are typically strong cationic compounds that interact strongly, e.g. covalently, with the negatively charged enzymes or microbial cells, leading to flocculation of the mixture. In general, they can be either low molecular weight compounds or polymers (either homopolymers or copolymers) bearing two or more sulfonium groups and optionally other cationic groups such as quaternary ammonium groups, with the molecular weight of the polymers being about 1,000 to 10,000,000, preferably 5,000 to 10,000,000. Advantageously, the sulfonium polymers should be water soluble or water dispersible. If they are used for both flocculation and cross-linking, the polymers containing sulfonium groups must be present in sufficient concentration to promote both flocculation and cross-linking upon heating and dehydration. Compounds most suitable for cross-linking and flocculation according to the subject invention are homopolymers or copolymers containing 2 or more reactive sulfonium groups. In the copolymer, the comonomer can be any monomer that copolymerizes with monomers containing sulfonium groups, but hydrophilic types, such as acryl amide, hydroxyethylacrylate, vinyl acetate, methyl acrylate, methyl methacrylate, acrylonitrile, acrylic acid and the like, are preferred due to the greater enzyme stability of the cross-linked product in an aqueous environment. The polymer may optionally include units bearing pendant hydrophobes such as vinyl benzyl dimethyl dodecyl ammonium and 9N10 methacrylate (9N10MA). Preferred sulfonium copolymers for use in the subject invention are as follows:

(1) 2-Hydroxyethyl methacrylate (often referred to as HEMA or 2-HEMA herein)/3-methyl-4-(vinylbenzyloxy) phenyl tetrahydrothiophenium (VIII) (U.S. Pat. No. 4,477,640).

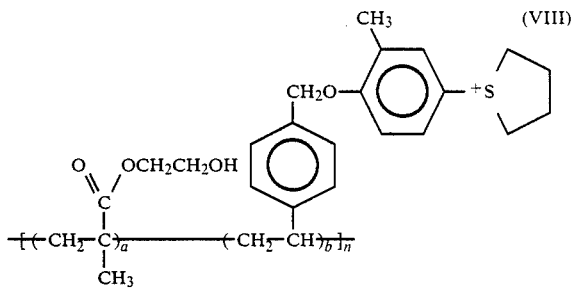

wherein a+b=1; and n represents an integer of from 10 through 10,000.

(2) HEMA/3-methacryloxyl-2-hydroxypropyl-3-hydroxy tetrahydrothiophenium (IX) (U.S. Pat. No. 4,444,977).

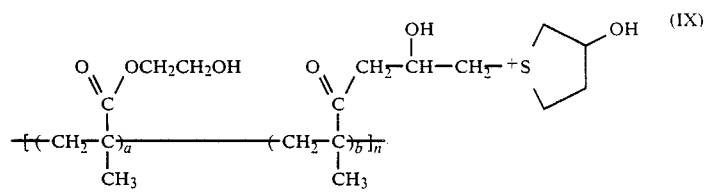

wherein a+b=1; and n represents an integer of from 10 through 10,000.

(3) HEMA/vinyl benzyl dimethyl sulfonium (VBS) (X) (U.S. Pat. No. 4,426,489)

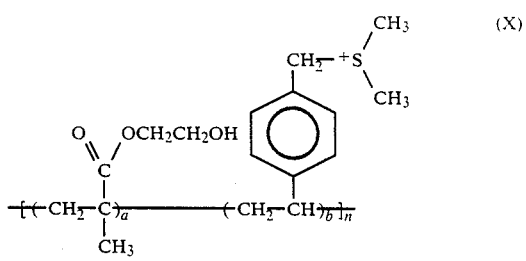

wherein a+b=1; and n represents an integer of from 10 through 10,000.

(4) Polymers containing vinyl benzyl dialkylsulfonium (VBS), aryl cyclic sulfonium or a vinyl benzyl sulfonium with 2 or more sulfonium groups and a pendant hydrophobe, such as: HEMA/VBS/9N10MA (XI)

cross-linking of the materials present in an aqueous environment, the bulk of the water is preferably removed prior to cross-linking. Dehydration continues during the cross-linking process.

The polyfunctional monomers having the following general formula are the most preferred group of cross-linkers:

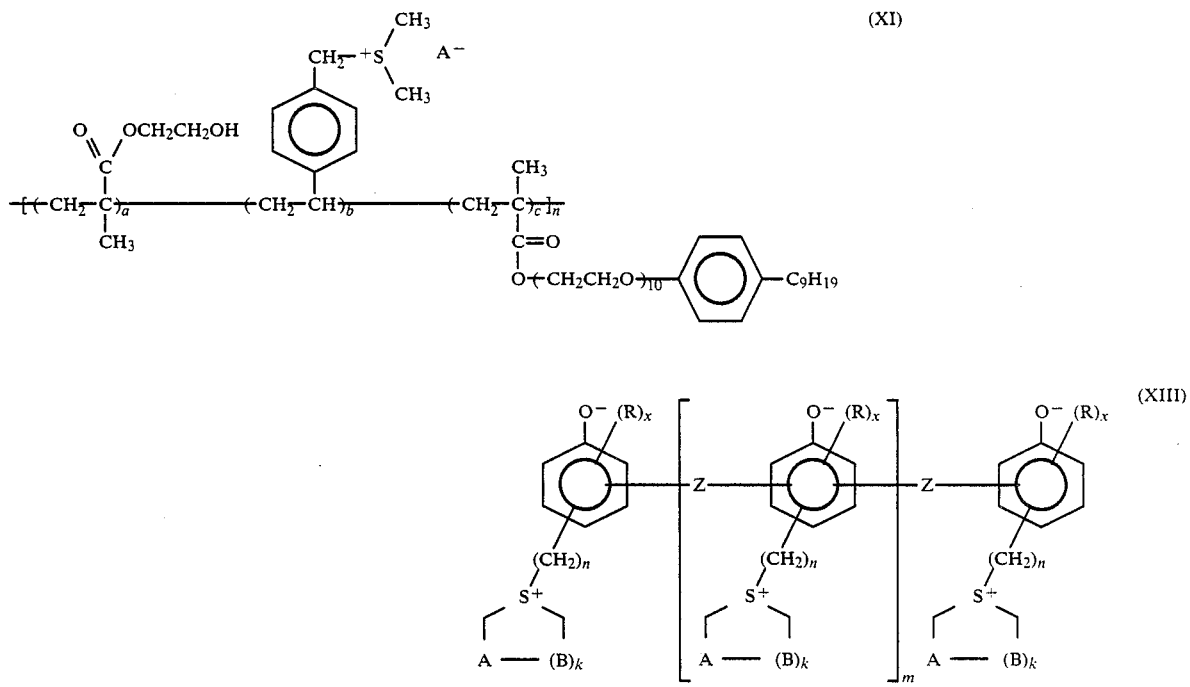

wherein a+b+c=1; n represents an integer of from 10 through 10,000; and $A^-$ represents any anion which does not interfere with cross-linking, for example, chloride or sulfate.

(5) Amphoteric polymers may be used either as crosslinkers when at or near the isoelectric point or as flocculants when at low pH, i.e., when the carboxyl groups remain unionized (as cationic polymers); an example is shown below:

HEMA/VBS/9N10MA/methacrylic acid (MAA)  (XII)

wherein Z represents a covalent bond, —O—, —S—, —CH$_2$—, —CHR'—, —CR'$_2$— where R' is (C$_1$-C$_4$) alkyl, or Z represents —O—(C$_a$H$_{2a-b}$(OH)$_b$)—O— where a is an integer from 1 through 6, and b is an integer of from 0 through 4; each R independently represents chloro, hydroxyl, (C$_1$-C$_4$) alkyl or (C$_1$-C$_4$) alkoxy; x represents an integer of from 0 through 2; n represents the integer 0 or 1; A and B each independently represent —CH$_2$— or —CHR"— where each R" independently represents hydrogen, hydroxyl or (C$_1$-C$_8$) alkyl; k represents the integer 1 or 2; and m is

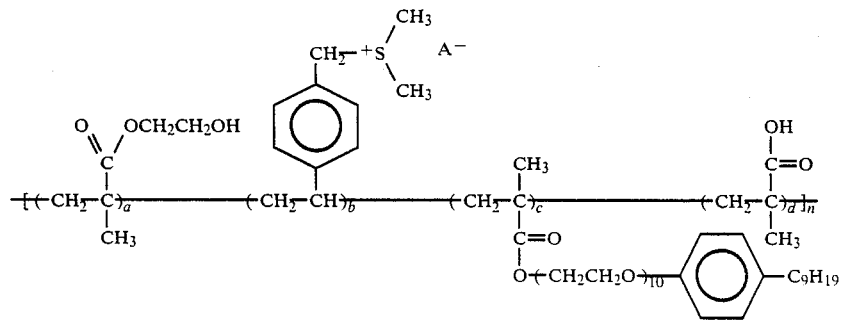

wherein a+b+c+d=1; n represents an integer of from 5 through 30; and $A^-$ represents any anion which does not interfere with cross-linking.

In summary, the improved immobilization process of the subject invention uses polysulfonium salts which can be monomeric, polymeric or copolymeric materials, including aryl, alkyl, cyclic or open chain sulfonium derivatives, as disclosed herein. In order to accelerate an integer of from 0 through 20. Preferably each sulfonium group is ortho or para to the phenoxide group. Particularly preferred are those cross-linkers where X is 0, n is 0, A is —CH$_2$— and k is 1.

Representative polyfunctional monomers within the scope of formula XIII include 1,1'-[(1-methylethylidene)bis(6-hydroxy-3,1-phenylene)]bis(tetrahydrothiophenium hydroxide)bis (inner salt) which is also referred to herein as bisphenol A sulfonium zwitterion (I); 1,1'-[dimethylene-bis(oxy-4-hydroxy-2,1-phenylene)]-bis-(tetrahydrothiophenium hydroxide)bis (inner salt); 1,1'-[methylene-bis(4-hydroxy-3,1-phenylene)]bis(tetrahydrothiophenium hydroxide)bis (inner salt); 1,1'-[(1-methylethylidene)-bis(6-hydroxy-3,1-phenylene)]bis(3-hydroxytetrahydrothiophenium hydroxide)bis(inner salt); and 1,1'-[(2,3,4,5-tetrahydroxyhexamethylene)-bis-(oxy-4-hydroxy-2,1-phenylene)]-bis(tetrahydrothiophenium hydroxide)bis (inner salt).

Various polymers are suitable as cross-linkers in accordance with the present invention. Depending on the molecular weight and the charge of the polymer, the polymers may be used as cross-linkers or as flocculants and cross-linkers. Polymers can be addition or condensation polymers, typically a copolymer of units containing sulfonium groups. Other monomer units also can be included in the polymer or copolymer to impart desirable properties to the final product.

Of the polymers suitable for use in the present invention, homopolymers or copolymers containing moieties such as the following are preferred:

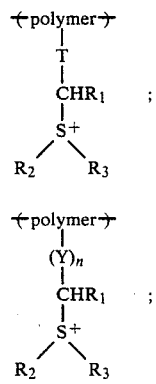

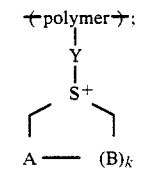

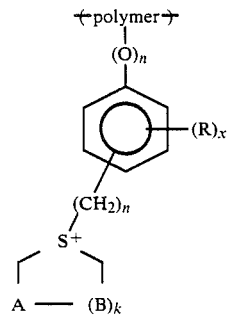

In the above moieties, T represents a connecting group, said connecting group being a divalent activating group that promotes reaction at the C—S bond to which it is joined, preferred connecting groups are vinylene, carbonyl, or phenylene optionally substituted with one or two substituents independently selected from chloro, hydroxyl, ($C_1$-$C_4$) alkyl, ($C_1$-$C_4$) hydroxyalkyl and ($C_1$-$C_4$) alkoxy; each $R_1$ independently represents hydrogen or methyl; $R_2$ and $R_3$ each independently represent ($C_1$-$C_4$) alkyl or ($C_1$-$C_4$) hydroxyalkyl; each Y independently represents T, ($C_1$-$C_4$) alkylene or ($C_1$-$C_4$) hydroxyalkylene; each n independently represents the integer 0 or 1; each R independently represents chloro, hydroxyl, ($C_1$-$C_4$) alkyl, ($C_1$-$C_4$) hydroxyalkyl or ($C_1$-$C_4$) alkoxy; x represents an integer of from 0 through 2; A and B each independently represent —$CH_2$— or —CHR''— in which each R'' is independently hydrogen, hydroxyl or ($C_1$-$C_8$) alkyl; and k represents the integer 1 or 2.

Polymers bearing the sulfonium moiety can be either addition or condensation polymers. Other monomer units can also be included in the polymer or copolymer to impart desirable properties to the final product.

Examples of suitable copolymers are as follows:

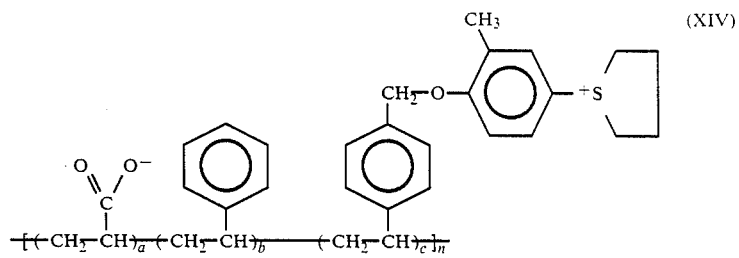

(XIV)

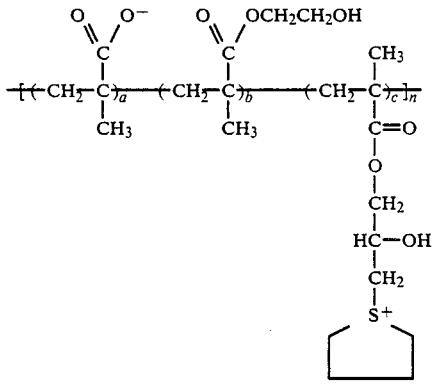

wherein formulas XIV and XV; a+b+c=1 and n represents an integer from 10 through 10,000.

The preparation of polyfunctional zwitterion monomers is described in U.S. Pat. Nos. 3,636,052; 3,723,386; 4,089,877; and Jour. Paint Tech. (1974) 46: No. 588, pp. 41–46. Also see Schmidt, D. L. (1977) ACS Symposium Series No. 59:318–331.

Suitable sulfonium polymers for use in the subject invention, and procedures for their preparation can be found in the patents and publications cited above and also in the following: U.S. Pat. Nos. 3,335,100; 3,544,499; 3,660,431; 3,767,622; 3,772,143; 3,804,797; 3,813,413; and 4,477,640.

Following are examples that illustrate the process and products of the invention. These examples should not be construed as limiting. All percentages are by weight and all solvent mixture proportions are by volume unless otherwise noted.

EXAMPLE 1

A suspension of whole cells of Ampullariella-3876, ATCC 31351, (200 ml; containing 3.54 percent solids), was adjusted to pH 8.0 with 5N potassium hydroxide. This suspension was stirred vigorously with a mechanical stirrer, while 1.8 milliliters (ml) of a diluted Purifloc C-31 ™ solution (containing 11 percent of active ingredient at pH 7) was added. Stirring continued for 1 minute at high speed and for 5 minutes at low speed. The flocculated cells were collected in a centrifuge bucket, (IEC chemical centrifuge, Damon/IEC Division, Needham Heights, Mass.) at 5200 revolutions per minute (rpm), and washed with 500 ml of distilled water. The cells were then subjected to heat treatment in a 70° C. oven for 1 hour. The flocculated and heat treated cells were extruded through a 0.03 inch (I.D.) exit tubing from a French Press (American Instrument Company, Silver Spring, Md.) at 4000 pounds per square inch (psi), and into an acetone bath (500 ml). The extrudate, after staying in acetone for about 1 hour, was allowed to dry in the air overnight. It was then pelletized in a Waring blender (3×5 second pulses) and screened for particles between 500 to 800 microns (i.e., the "particulates"), which were used for the cross-linking experiments.

The particulates (3.0 g) were weighed and placed in a 50-ml Erlenmeyer flask containing 6 ml of 0.2M potassium phosphate buffer at pH 8, and 1.2 ml of a 30 percent (w/v) aqueous solution of bisphenol A sulfonium zwitterion (I). This mixture was incubated in a shaker bath at 200 rpm and 50° C. for 1 hour, and dried in a vacuum oven at room temperature for 24 hours. The particulates were then dispersed in 50 ml of water, and washed with 3×50 ml of water, and 3×50 ml of acetone and again dried in the air overnight. Batch activity of the immobilized glucose isomerase was 177±19 GIU/g or 66 percent recovery of activity. Glucose isomerase activity expressed as GIU/g of IME [immobilized enzyme] is defined as micromoles of fructose formed per minute under standard conditions: 5 percent [w/v] glucose in 0.125M maleate buffer, containing 50 mM of $Mg^{++}$, 1 mM of $Co^{++}$ and 0.5 percent potassium chloride at pH 6.5 and 70° C.

The stability of the immobilized enzyme was determined in a continuous upflow column reactor at 70° C., using 50 percent (w/w) glucose as the substrate (CPC Dextrose containing 3 mM $Mg^{++}$ at pH 8). The rate of glucose isomerase inactivation calculated from its first order rate plot was $k_{inactivation} = 0.00283$/hr. corresponding to a half-life time ($t\frac{1}{2}$) of 245 hours.

EXAMPLE 2

The whole cells of Ampullariella-3876 were flocculated, heat treated, extruded and pelletized in the same manner as described in Example 1. The particulates of 300 to 500 microns were used for this experiment.

For cross-linking, 4 grams (g) of the particulates were weighed into a solution of 8 ml of 0.2M sodium borate buffer at pH 9 with 1.6 ml of a 30 percent (w/v) bisphenol A sulfonium zwitterion (I) solution. The mixture was incubated at 70° C. for 5 hours, dried in a vacuum oven for 24 hours at room temperature and worked up as described in Example 1. The glucose isomerase activity was found to be 224±12 GIU/g with a $k_{inactivation} = 0.00299$/hr corresponding to a $t\frac{1}{2} = 231$ hours.

EXAMPLE 3

A suspension of ruptured cells of Ampullariella-3876 (500 ml; pH 8.0 containing 3.06 percent solid) was flocculated with 209 ml of 1.1 percent Purifloc C-31 ™. The flocculated cell mash was collected, heat treated, extruded and pelletized, and the particles of 300–500 micron size (the "particulates") were used for cross-linking.

The particulates (8.0 g) were weighed into 16 ml of 0.2N sodium borate buffer at pH 9.0 containing 3.84 ml of a 25 percent (w/v) bisphenol A sulfonium zwitterion solution (I). This material was incubated at 70° C. in a shaker bath at 200 rpm for 1 hour, and dried in a 70° C. vacuum oven for 3 hours. It was then washed and dried to yield immobilized ruptured cells of Ampullariella-3876 having a glucose isomerase activity of 203±27 GIU/g; (64 percent recovery) and a half-life time of 198 hours, as determined by a column study similar to that described in Example 1.

EXAMPLE 4

A suspension of cells of Ampullariella-3876 (100 ml, containing 3.03 percent solids) was adjusted to pH 8.0 with 5N potassium hydroxide. This suspension was stirred vigorously while a solution of the copolymer (XIa) (7 ml containing 15.7 percent solids or an amount equivalent to 36 percent of cell mass) was added. The flocculated cells were collected in a chemical centrifuge bucket (ICI Chemical Centrifuge, Damon/IEC Division, Needham Heights, Mass.) at 5200 rpm, and washed with 1 liter of distilled water.

The flocculated cell paste was extruded through a 0.03 inch exit tubing from a French press (American Instrument Company, Silver Spring, Md.) at 4000 psi into an acetone bath (100 ml). The extrudate, after being left in the acetone for 1 hour, was removed and allowed to dry in the air overnight. It was pelletized in a Waring blender and screened to select particles of 500 to 800 microns (the "particulates") in size. To cross-link, the particulates were heated at 70° C. in a vacuum oven for 1 hour. The product had a glucose isomerase activity of $142 \pm 12$ GIU/g (or 70 percent of the initial activity) and excellent dry strength.

EXAMPLE 5

A procedure similar to that described in Example 4 was used. Two hundred ml of a suspension of cells of Ampullariella-3876 (4.93 percent solids) was flocculated with copolymer (XIIa) (25 ml containing 3.2 percent polymer). The flocculated cell paste (92.5 percent of cells) was extruded, pelletized and heated at 70° C. in a vacuum oven for 1 hour. The fraction of 500 to 800 micron particles was used for an activity assay and a stability study using a column reactor and a procedure similar to that in Example 1. The product had a glucose isomerase activity of $182 \pm 3$ GIU/g (71 percent retention of activity), and a $k_{inactivation} = 0.0052/hr$ corresponding to a $t_{\frac{1}{2}}$ of 133 hours.

EXAMPLE 6

According to the procedure described in Example 5, 500 ml of cell suspension of Ampullariella-3876 (12.88 g solid) was flocculated with 50 ml of 12.6 percent of a copolymer of 2-HEMA:VBS+:9N10MA (80:10:10) (nXX=30) (0.49 g of polymer per g of cell). The particles were formed and cross-linked to yield immobilized enzyme particles with a glucose isomerase activity of $124 \pm 6$ GIU/g (70 percent retention of activity) and $k_{inactivation} = 0.0042/hr$, corresponding to a $t_{\frac{1}{2}}$ of 165 hours.

EXAMPLE 7

Ampullariella-3876 (200 ml containing 4.93 percent solid) was flocculated with 10 ml of 3.1 percent of copolymer (XIa) according to the procedure described in Example 4. The flocculated cells (97 percent cells and 3 percent copolymer (XIa) were collected and washed with 2 liters of distilled water in a centrifuge bucket. In order to determine whether the presence of additional carboxyl groups impacted on the cross-linking of the Ampullariella-3876 cells, 10 grams of the flocculated cell paste containing 17.24 percent solids) were mixed well with 2 g of a polymer solution containing 3.05 percent of a 2-HEMA:9N10MA:MAA (80:10:10) copolymer (herein Copolymer A). This was extruded, pelletized and screened. The particles ranging from 500 to 800 microns were heated and dried at 70° C. in a vacuum oven for 1 hour. The product had a final composition of Ampullariella-3876:copolymer (XIa):copolymer A of 94:3:3, a glucose isomerase activity of $212 \pm 21$ GIU/g (85 percent of the initial activity) and $k_{inactivation} = 0.0062/hr$ corresponding to a $t_{\frac{1}{2}}$ of 112 hours.

EXAMPLE 8—ENZYME IMMOBILIZATION OF PAPER PULP

A suspension of Ampullariella-3876 (400 ml; containing 3 percent of dry cellular matter) was mixed with 400 ml of a paper pulp slurry (1.64 percent solid; Federal Bleached Softwood Kraft pulp). This was stirred vigorously while a solution of 40 ml of copolymer (XIIa) (containing 3.18 percent of the polymeric material) was added. Stirring was continued for 1 minute, and the flocculated mixture was then poured into 14 liters of deionized water in a paper-making apparatus to form a sheet of immobilized enzyme paper ($10 \times 10$ inches). This was placed on a filter paper and pressed dry between 2 layers of virgin wool. The immobilized enzyme paper was further dried and cured at 70° C. for 1 hour, and was assayed for its glucose isomerase activity under standard conditions. It had an activity of $103 \pm 5$ GIU/g of immobilized enzyme (IME), or 63 percent recovery of the initial activity, and a composition of Ampullariella cells:pulp:copolymer (XIIa) of 70:23:7. Stability of the immobilized enzyme was tested in a column reactor at 70° C. as in Example 1. The initial rate of glucose isomerase inactivation (the $k_{inactivation}$) was 0.00192/hr, corresponding to a $t_{\frac{1}{2}}$ of 391 hours.

EXAMPLE 9

In a procedure similar to the procedure described in Example 8, Amullariella cells were immobilized on paper pulp using copolymer (XIa) as the flocculant and cross-linker. In this procedure, 200 ml of the cell suspension and 200 ml of the wood pulp slurry were mixed and 10 ml of a solution of the copolymer (containing 3.14 percent of copolymer (XIa)) was introduced. This mixture was cast into a sheet of paper ($10 \times 10$ inches) with the Ampullariella cells immobilized on it (the "immobilized enzyme paper"). Upon curing and drying the immobilized enzyme paper for 1 hour at 70° C., the immobilized enzyme had an activity of $119 \pm 8$ GIU/g of IME; or 79 percent recovery of the enzyme activity. The preparation contained 63 percent bacteria cells, 34 percent wood pulp and 3 percent sulfonium copolymer. Its first half-life time, determined in a column reactor at 70° C. and pH 7.4 was 259 hours, which corresponds to a $k_{inactivation} = 0.00268/hr$.

EXAMPLE 10

In a procedure similar to the procedure of Example 8, cells of Ampullariella-3876 (73 parts) were immobilized on paper pulp (24 parts) using Purifloc C-31 TM (3 parts) as the flocculant. After the paper was cast and dried, a section (approximately 25 square inches and weighing 4 g) was sprayed uniformly with a solution of cross-linking reagent; the cross-linking reagent contained 0.48 g of a bisphenol A sulfonium zwitterion (I) in 8 ml of a sodium borate buffer (0.2N, pH 9). The sprayed paper was allowed to dry in a vacuum oven at 50° C. for 1 hour. The initial inactivation rate was determined to be $k_{inactivation} = 0.0026/hr$, corresponding to a $t(\frac{1}{2})$ of 266 hours.

EXAMPLE 11

Cells of Ampullariella-3876 were fluocculated with Purifloc C-31 ™ and immobilized on paper as described in Example 10. The flocculated cells were subsequently cross-linked with glutaraldehyde, to compare the effectiveness of glutaraldehyde cross-linking, by uniformly spraying both sides of the cell-paper composite (approximately 25 sq. in., 4 g) with a solution containing 0.48 g of glutaraldehyde in 12 ml of a 0.1N potassium phosphate buffer at pH 8.0. The sprayed cell-paper composite was dried at room temperature overnight. The glucose isomerase activity was found to be 38 GIU/g of the immobilized glucose isomerase or 24 percent recovery of the initial activity. No stability study was conducted due to the low glucose isomerase activity.

In the preceding examples,

Table 2 shows a comparison of several polysulfonium cross-linkers.

Table 3 shows a comparison of cross-linking reactions at various conditions; the percentages of flocculant and the bisphenol A sulfonium cross-linker (I), and pH, being the variables.

Table 4 lists the compositions and concentrations of polysulfonium copolymers used for the immobilization of Ampullariella-3876.

TABLE 1

Comparison of Glutaraldehyde and Sulfonium Zwitterion* Crosslinking of *Ampullariella* - 3876

|  | Glutaraldehyde | Sulfonium Zwitterion |
|---|---|---|
| Activity recovery (yield) | 30-50 percent | 60-90 percent |
| Reaction conditions | room temperature 30-60 minutes | 50-70° C., and dried *in vacuo* |
| pH | ~8 | 8-10 |
| Concentration required | >15 percent | 4-20 percent |
| Physical integrity | compressed readily | more rigid and has good flow properties |

*Bisphenol A Sulfonium Zwitterion (I)

Bisphenol A Sulfonium Zwitterion (I):

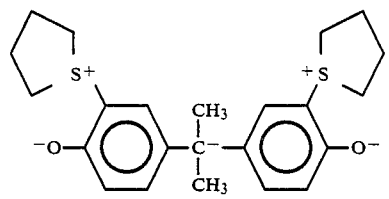

Copolymer XIa:

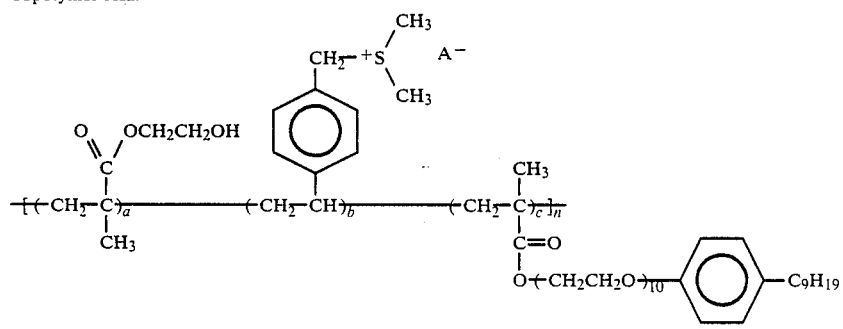

where $a=0.5$, $b=0.4$, $c=0.1$, $A^-=Cl^-$ and $n=XX30$

Copolymer XIIa:

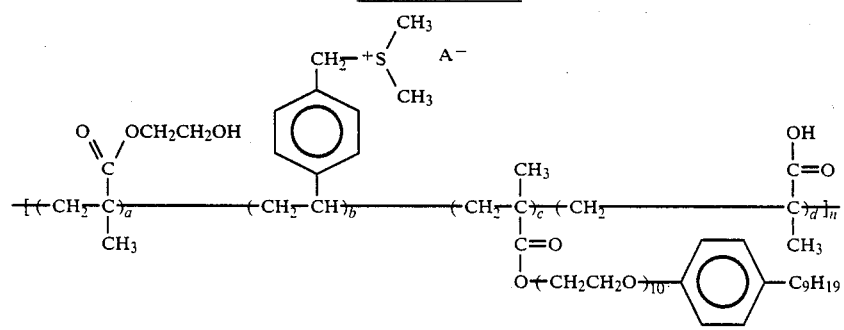

where $a=0.55$, $b=0.25$, $c=0.1$, $d=0.1$, $A^-=Cl^-$ and $n=XX30$

Table 1 shows a comparison of glutaraldehyde and bisphenol A sulfonium Zwitterion (I) cross-linking of Ampullariella-3876.

TABLE 2

Sulfonium Crosslinkers[a]

| Compound | pH of Crosslinking | Activity (GIU/g) | % Recovery |
|---|---|---|---|
| [structure: bis(tetrahydrothiophenium) bisphenol with C(CH$_3$)$_2$ bridge] | 8<br>9 | 177 ± 19<br>249 ± 17 | 66<br>93 |
| [structure: bis(tetrahydrothiophenium) with -O(CH$_2$)$_3$O- bridge] | 8<br>9 | 183 ± 8<br>252 ± 13 | 68<br>94 |
| [structure: biphenyl bis(tetrahydrothiophenium) diol] | 8<br>9 | 203 ± 18<br>257 ± 8 | 76<br>96 |
| [structure: bis(tetrahydrothiophenium) with -CH$_2$- bridge] | 8<br>9 | 208 ± 3<br>237 ± 18 | 78<br>88 |

[a]The immobilization was carried out in the same manner as described in Example 1.

TABLE 3

Sulfonium Crosslinking of Ampullariella[a]

| Run No. | pH | Percent Flocculant[d] | Percent Zwitterion | Activity GIU/g | Compression Strength,[b] lbs | Relative Rate of Inactivation[c] $k_{inact}/k_{inact}$ of Sweetzyme Q |
|---|---|---|---|---|---|---|
| 1 | 9 | 4 | 12 | 159 | 1.26 | 1.02 |
| 2 | 10 | 6 | 18 | 128 | 2.36 | 1.56 |
| 3 | 10 | 2 | 18 | 138 | 1.53 | 1.22 |
| 4 | 10 | 6 | 6 | 185 | 2.36 | 1.08 |
| 5 | 10 | 2 | 6 | 191 | 1.20 | 1.16 |
| 6 | 8 | 6 | 18 | 157 | 0.91 | — |
| 7 | 8 | 2 | 18 | 183 | 1.23 | 1.40 |
| 8 | 8 | 6 | 6 | 178 | 1.29 | 1.02 |
| 9 | 8 | 2 | 6 | 181 | 1.56 | 1.16 |
| 10 | 9 | 4 | 12 | 154 | 1.15 | 1.23 |
| 11 | 10.2 | 4 | 12 | 152 | 1.12 | 0.88 |
| 12 | 9 | 6.4 | 12 | 165 | 1.77 | 1.16 |
| 13 | 9 | 4 | 19.3 | 117 | 1.54 | 1.69 |
| 14 | 7.8 | 4 | 12 | 165 | 1.78 | 1.17 |
| 15 | 9 | 1.6 | 12 | 233 | 1.50 | 1.63 |
| 16 | 9 | 4 | 4.7 | 192 | 1.46 | 1.00 |

TABLE 3-continued
Sulfonium Crosslinking of Ampullariella[a]

| Run No. | pH | Percent Flocculant[d] | Percent Zwitterion | Activity GIU/g | Compression Strength,[b] lbs | Relative Rate of Inactivation[c] $k_{inact}/k_{inact}$ of Sweetzyme Q |
|---|---|---|---|---|---|---|
| 17 | 9 | 4 | 12 | 180 | 1.76 | 1.36 |

[a]The crosslinking, using Bisphenol A Sulfonium Zwitterion (I), was carried out at 70° C. for 3 hours followed by drying at room temperature in a vacuum oven overnight.

[b]Compression strength was reported as pounds of weight load at failure. Measured on an Instron Universal Tester (Instron Corp.)

[c]Relative rate of inactivation is expressed as rate of inactivation compared to that of Sweetzyme Q (commercial product available through Novo Industries A/S, Bagsvaerd, Denmark). Immobilized systems with relative rates of inactivation <1, decay more slowly than Sweetsyme Q; >1, more quickly than Sweetzyme Q; or 1, at the same rate as Sweetzyme Q.

[d]Flocculant Used: Purifloc C-31 ™.

TABLE 4
Flocculation and Crosslinking of Ampullariella - 3876 with Sulfonium Copolymers*

| Copolymers of | Amount Added Wt%[a] | Glucose Isomerase Activity GIU/g |
|---|---|---|
| 2-HEMA:VBS+Cl− (75:25) | 25 | 91±5 |
|  | 16 | 168±1** |
| 2-HEMA:VBS+Cl−:9N10MA (80:10:10) | 10 | 122±23 |
|  | 5 | 124±6 |
| 2-HEMA:VBS+Cl−:9N10MA (70:20:10) | 18 | 102±20 |
| 2-HEMA:VBS+Cl−:9N10MA (60:30:10) | 16 | 130±10 |
| 2-HEMA:VBS+Cl−:9N10MA (50:40:10) | 36 | 142±12 |
|  | 2.6 | 167±8** |
| 2-HEMA:VBS+Cl−:9N10MA:MAA (55:25:10:10) | 23 | 131±7 |
|  | 12 | 145±6** |
|  | 7.5 | 182±3 |
| 2-HEMA:VBS+Cl−:9N10MA:MAA (63:17:10:10) | 35 | 83±17 |
|  | 2.1 | 175±18 |

[a]Based on dry weight of Ampullariella - 3876.
*The experimental procedure used was similar to that of Example 4; the copolymers used in the testing had a molecular weight in the range of about 5,000 to 100,000.
**Crosslinking at 55° C. in a vacuum oven.

As used herein,

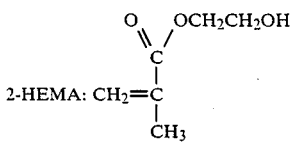

2-HEMA

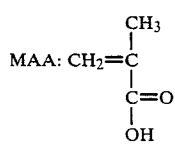

MAA

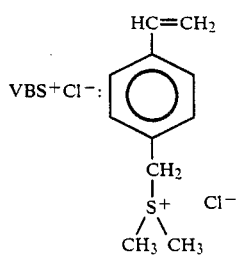

VBS+Cl−

-continued

9N10MA:

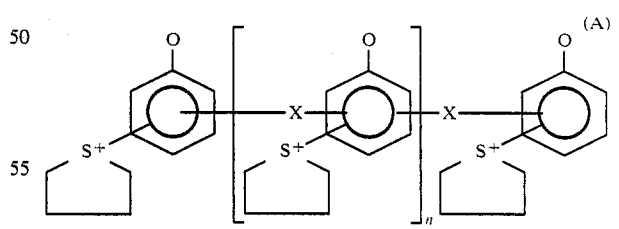

What is claimed is:

1. A process for immobilizing an enzyme or cellular material containing said enzyme which comprises:
   (a) forming a mixture by contacting said enzyme or cellular material with a water-compatible, chemically reactive polysulfonium salt selected from the group consisting of

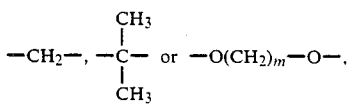

(A)

wherein:
n represents an integer of from 0 through 5;
X represents a covalent bond, $$-CH_2-, \quad -\underset{\underset{CH_3}{|}}{\overset{\overset{CH_3}{|}}{C}}- \quad \text{or} \quad -O(CH_2)_m-O-,$$

in which m is an integer of from 1 through 6; and

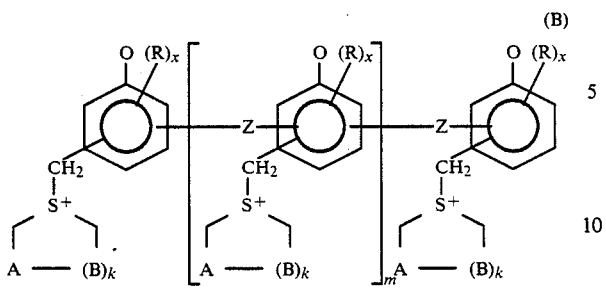

wherein:

Z represents a covalent bond, —O—, —S—, —CH$_2$—, —CHR'—, —CR'$_2$—, where R' is C$_1$–C$_4$ alkyl, or Z represents —O—[C$_a$H$_{2a-b}$(OH)$_b$]—O— where a is an integer from 1 through 6, and b is an integer of from 0 through 4;

each R independently represents chloro, hydroxyl, C$_1$–C$_4$ alkyl or C$_1$–C$_4$ alkoxy; x represents an integer of from 0 through 2; A and B each independently represent —CH$_2$— or —CHR"—, where each R" independently represents hydrogen, hydroxyl or C$_1$–C$_8$ alkyl; k represents the integer 1 or 2; and m is an integer of from 0 through 20; and (C) a polysulfonium salt polymer containing 2 or more reactive sulfonium groups selected from the group consisting of

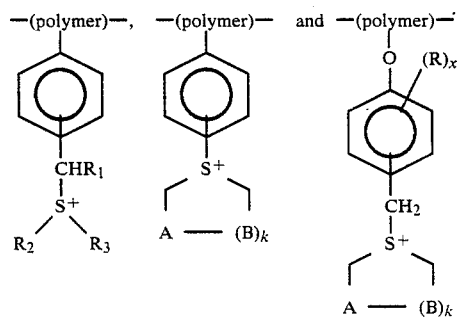

wherein:
R$_1$ independently represents hydrogen or methyl;

R$_2$ and R$_3$ each independently represent C$_1$–C$_4$ alkyl or C$_1$–C$_4$ hydroxyalkyl;

R independently represents chloro, hydroxyl, C$_1$–C$_4$ alkyl, C$_1$–C$_4$ hydroxyalkyl or C$_1$–C$_4$ alkoxy;

x represents an integer of from 0 through 2;

A and B each independently represent —CH$_2$— or —CHR"— in which R" is independently hydrogen, hydroxyl or C$_1$–C$_8$ alkyl; and k represents the integer 1 or 2; and (b) subjecting the mixture to conditions wherein the sulfonium ions react with nucleophilic groups contained by the enzyme or cellular material present in the mixture to form covalently cross-linked and water-insoluble products.

2. The process of claim 1 wherein the enzyme is glucose isomerase.

3. The process of claim 1 wherein the enzyme or cellular material containing said enzyme is first flocculated and then contacted with the polysulfonium salt.

4. The process of claim 1 wherein the polysulfonium salt is selected from the group consisting of 1,1'-[(1-methylethylidene)bis(6-hydroxy-3,1-phenylene)]bis(tetrahydrothiophenium hydroxide)bis (inner salt); 1,1'-[dimethylene-bis(oxy-4-hydroxy-2,1-phenylene)]bis(tetrahydrothiophenium hydroxide)bis (inner salt); 1,1'-]methylene-bis(4-hydroxy-3,1-phenylene)]bis(tetrahydrothiophenium hydroxide)bis (inner salt); 1,1'-[(1-methylethylidene)-bis(6-hydroxy-3,1-phenylene)]bis-(3-hydroxytetrahydrothiophenium hydroxide)bis (inner salt); and 1,1'-[(2,3,4,5-tetrahydroxyhexamethylene)bis-(oxy-4-hydroxy-2,1-phenylene)]bis(tetrahydrothiophenium hydroxide)bis (inner salt).

5. The process of claim 1 wherein the polysulfonium salt is 1,1'-[(1-methylethylidene)bis(6-hydroxy-3,1-phenylene)]bis(tetrahydrothiophenium hydroxide)bis (inner salt).

6. An enzyme-containing water-insoluble product prepared as claimed in claim 1.

7. The product of claim 6 in the form of a water-swollen particle.

8. The product of claim 6 wherein the product is on paper.

9. The product of claim 6 wherein the enzyme is glucose isomerase.

10. The product of claim 9 wherein the enzyme is produced by Ampullariella-3876, ATCC 31351.

* * * * *